United States Patent [19]
Gardner et al.

[11] 3,950,446
[45] Apr. 13, 1976

[54] PROCESS FOR PRODUCING ETHYNYLATING AGENTS

[75] Inventors: John Nicholson Gardner, Garrison, N.Y.; George McClelland Whitesides, Newton, Mass.

[73] Assignee: Hoffmann-La Roche Inc., Nutley, N.J.

[22] Filed: Apr. 15, 1974

[21] Appl. No.: 460,847

[52] U.S. Cl. .......................... 260/665 R; 260/638 Y
[51] Int. Cl.² ............................................. C07F 3/02
[58] Field of Search ............. 260/665 G, 665 R, 665

[56] References Cited
UNITED STATES PATENTS

| | | |
|---|---|---|
| 3,441,621 | 4/1969 | Tedeschi et al. ................. 260/665 R |
| 3,766,280 | 10/1973 | Kamienski et al. ............. 260/665 R |
| 3,770,655 | 11/1973 | Vandenberg ................ 260/665 R X |

OTHER PUBLICATIONS

Chemical Abstracts, Vol. 64, 17623b (1966).
Chemical Abstracts, Vol. 35, 54573 (1941).
Chemical Abstracts, Vol. 63, 17908e (1965).

*Primary Examiner*—Helen M. S. Sneed
*Attorney, Agent, or Firm*—Samuel L. Welt; Jon S. Saxe; Richard A. Gaither

[57] ABSTRACT

An ethynylating agent formed from mixing an anhydrous magnesium compound with sodium acetylide and its use in preparing ethynyl carbinols.

5 Claims, No Drawings

PROCESS FOR PRODUCING ETHYNYLATING AGENTS

BACKGROUND OF THE INVENTION

In the past, ethynyl carbinols of the formula:

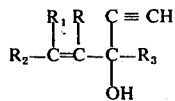

wherein $R_1$ is lower alkyl, lower alkenyl or hydrogen; $R_2$ is hydrogen or a hydrocarbon having from 1 to 18 carbon atoms; $R_1$ and $R_2$ taken together with their attached carbon atom form a cyclic member selected from the group consisting of cyclo lower alkyl, or cyclo lower alkenyl; and R and $R_3$ are lower alkyl, lower alkenyl or hydrogen; have been formed by reacting a compound having the formula:

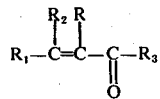

wherein R, $R_1$, $R_2$ and $R_3$ are as above; with an ethynylating agent such as sodium acetylide. See J.A.C.S. 57, p. 340, (1935); and J.A.C.S. 61, 1289 (1944). The use of sodium acetylide as an ethynylating agent has proven disadvantageous since the yields of the compound of formula I have been low. In U.S. Pat. No. 2,425,201, Oroshnik, Aug. 5, 1947, the use of calcium acetylide for carrying out this process is disclosed. Furthermore, in Oroshnik et al., J.A.C.S. 71, 2062 (1949), the use of acetylides such as lithium acetylide, potassium acetylide and calcium acetylide for carrying out this reaction has been disclosed. However, these acetylides have proven to be very expensive. Furthermore, when these acetylides are utilized as an ethynylating agent, the compound of formula I is produced together with various side products and tars which are difficult to separate from the compound of formula I. Therefore, a more economical ethynylating agent which will produce the compound of formula I in high yields without difficulty separable tars and side products has been long desired in the art.

SUMMARY OF THE INVENTION

In accordance with this invention it has been discovered that when an ethynylating agent formed by mixing sodium acetylide with an anhydrous magnesium compound selected from the group consisting of magnesium chloride, magnesium sulfate, magnesium fluoride and an organo magnesium halide in liquid ammonia, is reacted with the compound of formula II in liquid ammonia, the compound of formula I is prepared in high yields without the substantial formation of difficulty separable side products and tars.

The use of this ethynylating agent formed from the mixture of the magnesium compound with sodium acetylide vastly improves the process of forming the compound of formula I by reacting an acetylene or an acetylide with the compound of formula II. The vast improvement is obtained by utilizing an ethynylating agent formed from a magnesium compound with sodium acetylide. This can be seen by the fact that the yields of about 30% of the compound of formula I are obtained when sodium acetylide is utilized as the ethynylating agent whereas yields of about 70% or greater are obtained when the ethynylating agent of this invention is utilized in this reaction.

DETAILED DESCRIPTION OF THE INVENTION

The lower alkyl groups which, in formulae I and II, are represented by the symbols R, $R_1$ and $R_3$ include, for example, straight or branched chain alkyl groups containing from 1 to 7 carbon atoms, such as methyl, ethyl, propyl, isopropyl, butyl, isobutyl, pentyl, hexyl, heptyl, etc. radicals. The lower alkenyl groups which in formulae I and II are represented by the symbols R, $R_1$ and $R_3$ include, for example, straight or branched chain alkenyl groups containing from 2 to 7 carbon atoms sch as ethenyl, propenyl, 1-butenyl, 1-pentenyl, 2-pentenyl. The term "halogen" includes all four halogens i.e., bromine, chlorine, fluorine and iodine with bromine and chlorine being preferred.

The hydrocarbon radical $R_2$ in formulae I and II includes aliphatic, cycloaliphatic or aromatic hydrocarbon radicals, having from 1 to 18 carbon atoms. The aliphatic hydrocarbon radical may be saturated or unsaturated. Thus, for example, the hydrocarbon radical can be an alkyl group having from 1 to 18 carbon atoms, such as a methyl, ethyl, propyl, isopropyl, butyl, isobutyl, hexyl, octyl, decyl, undecyl, dodecyl, tetradecyl, pentadecyl, heptadecyl, octadecyl, etc. radical. Moreover, the hydrocarbon radical represented by the symbol $R_2$, indicates alkynyl or alkenyl groups, either straight or branched chain, having from 2 to 18 carbon atoms, such as ethynyl, propynyl, 1-butynyl, 2-butynyl, 1-pentynyl, 2-pentynyl, 2-methyl-2-pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, etc. radicals. The 4,8-dimethyl nonadien-3,7-yl group is exemplary of another hydrocarbon radical which is represented in formulae I and II by the symbol $R_2$.

When $R_2$ is aromatic hydrocarbon radical, this radical includes aromatic hydrocarbon radicals containing from 6 to 18 carbon atoms such as phenyl, lower alkyl substituted phenyl (which include o-tolyl, m-tolyl, etc.) naphthyl, phenyl substituted aliphatic hydrocarbons such as benzyl, phenethyl, etc. $R_2$ can be a cycloaliphatic hydrocarbon containing from 3 to 18 carbon atoms. Among the preferred cycloaliphatic radicals are the cyclo-lower alkyl radicals which contain a cyclic ring structure of from 3 to 7 carbon atoms such as cyclopropyl, cyclohexyl, etc. and the cyclo-lower alkenyl radical containing a cyclic ring structure of from 3 to 7 carbon atoms such as cyclohexenyl, and cycloheptenyl. The cycloalkenyl or cyclo-lower alkyl moieties can be unsubstituted or substituted in one or more positions with a lower alkyl group. The cycloaliphatic substituted aliphatic hydrocarbon radicals can contain from 4 to 18 carbon atoms such as cyclohexyl-methyl, cyclohex-1-en-yl-penta-2,6-dien, etc.

Finally, taken together the symbols $R_1$ and $R_2$ of formulae I and II represent cycloalkyl groups, preferably cyclo-lower alkyl groups containing a cyclic ring structure of from 3 to 7 carbon atoms such as cyclopropyl cyclobutyl, cyclopentyl, cyclohexyl, etc. groups or cycloalkenyl groups, preferably, cyclo-lower alkenyl groups containing a ring having from 3 to 7 carbon atoms, such as cyclopropenyl, cyclobutenyl, cyclopentenyl, cyclohexenyl, etc. groups. The cyclo-lower alkyl or cyclo-lower alkenyl groups can be substituted in one or more positions with a lower alkyl group. Generally, these cyclo-lower alkyl or cyclo-lower alkenyl groups contain from 3 to 18 carbon atoms.

The term "aryl" signifies mononuclear aromatic hydrocarbons such as phenyl, tolyl, etc. which can be unsubstituted or substituted in one or more positions with lower alkyl substituents. Also the term "aryl" signifies polynuclear aromatic hydrocarbon groups such as naphthyl, anthryl, phenanthryl, azulyl, etc., which can be unsubstituted or substituted with one or more of the lower alkyl groups. The preferred aryl substituents are phenyl or naphthyl, which can be substituted or unsubstituted in one or more positions with lower alkyl.

In accordance with this invention, the ethynylating agent is prepared by mixing, under anhydrous conditions, sodium acetylide and a magnesium compound selected from the group consisting of magnesium chloride, magnesium fluoride, magnesium sulfate or an organo magnesium halide in liquid ammonia. In forming this ethynylating agent, the sodium acetylide can be present in the mixture in an amount of at least 10% by weight, based upon the total weight of the magnesium in the magnesium compound and the sodium acetylide in the mixture. If desired, any amount of sodium acetylide higher than 10% by weight, based upon the total weight of the magnesium in the magnesium compound and the sodium acetylide in the mixture, can be utilized. The formation of the ethynylating agent is generally carried out with from about 10% to 95% by weight of sodium acetylide, based upon the weight of sodium acetylide and magnesium in the magnesium compound and from 5% by weight to 90% by weight of the magnesium in the magnesium compound, taken on the same basis. Generally, it is preferred to utilize from about 40% by weight to about 60% by weight of the sodium acetylide and about 40% by weight to 60% by weight of the magnesium in the magnesium compound, said weight % based upon the total weight of magnesium in the magnesium compound and sodium acetylide.

As the magnesium compound, an organo magnesium halide can be utilized. These compounds are conventional Grignard reagents. Therefore, any of the conventional Grignard reagents can be utilized as the organo magnesium halide. Since the organo group does not enter into the formation of the ethynylating agent or into the ethynylating reaction, the precise nature of this group is unimportant. Among the conventional organo magnesium compounds which can be utilized in forming the ethynylating agent of this invention, are included aryl magnesium halides, lower alkyl magnesium halides, cycloalkyl magnesium halides, etc. Among the preferred organo magnesium halides are included phenyl magnesium chloride, ethyl magnesium chloride, isopropyl magnesium chloride and tolyl magnesium chloride.

The ethynylating agent of this invention is prepared by mixing, under anhydrous conditions, sodium acetylide and the magnesium compound in liquid ammonia. The sodium acetylide can, if desired, be formed in liquid ammonia prior to the addition of the magnesium compound. The sodium acetylide can be prepared by conventional means prior to the addition of the magnesium compound to the reaction medium. In accordance with a preferred embodiment of this invention, the sodium acetylide is formed by passing acetylene into the liquid ammonia reaction medium containing sodium either in its metal or sodamide form. After the sodium acetylide has been formed in this manner, the magnesium compound can be added to the liquid ammonia reaction medium to form the ethynylating agent of this invention.

In forming the ethynylating agent of this invention, any combination of temperatures and pressures sufficient to keep the ammonia in a liquid state can be utilized. Generally in carrying out this formation, temperatures of from −100°C. to +100°C. with pressures of from about 15 lbs. per square inch absolute to 1,000 lbs. per square inch absolute can be utilized. Generally it is preferred to utilize temperatures of from −50°C. to +25°C. and pressures of from 15 lbs. per square inch absolute to 150 lbs. per square inch absolute in carrying out this reaction. The formation of the ethynylating agent should be carried out under substantially anhydrous conditions. Therefore, the magnesium compound which is used in this formation should be in the anhydrous state.

Upon mixing the sodium acetylide with the magnesium compound, the ethynylating agent forms. This ethynylating agent forms as a precipitate which precipitate can be recovered in solid form from the reaction medium by conventional means such as filtration. The exact nature of this solid ethynylating agent cannot be determined, however it is believed to be a reaction product between the sodium acetylide and the magnesium compound.

On the other hand, the ethynylating agent need not be isolated from the liquid ammonia reaction medium. This is true since the liquid ammonia reaction medium can be utilized as the reaction medium for converting the compound of formula II to the compound of formula I.

In accordance with this invention, the reaction of the compound of formula II to form the compound of formula I is carried out with the aforementioned ethynylating agent in a liquid ammonia reaction medium. If desired, both the compound of formula II and the ethynylating agent can be added to the liquid ammonia reaction medium. On the other hand, it is preferred to carry out this reaction in the liquid ammonia reaction medium in which the ethynylating agent is formed. In this manner, the ethynylating agent need not be isolated from the liquid ammonia reaction medium in which it was formed. Therefore, in accordance with the preferred embodiment of this invention, the compound of formula II is added to the reaction medium after the formation of the ethynylating agent and is converted to the compound of formula I therein. In carrying out this reaction, any combination of temperature and pressure which is sufficient to keep the ammonia in a liquid state can be utilized. In carrying out this reaction, temperatures of from about −100°C. to +100°C. with pressures of from about 15 p.s.i.a. to about 1,000 p.s.i.a. can be utilized. Generally, it is preferred to utilize temperatures of from −50°C. to +25°C. and pressures of from 15 p.s.i.a. to 150 p.s.i.a. in carrying out this reaction.

In addition to the liquid ammonia, an inert organic solvent can be present in the reaction medium if desired. Conventional inert organic solvent can be present in the reaction medium in addition to liquid ammonia. Among the solvents which may be utilized are diethyl ether and toluene. If desired, the reaction of the compound of formula II to the compound of formula I can be carried out in the presence of acetylene gas in the reaction medium. Therefore, if excess acetylene was utilized to form the sodium acetylide utilized in the ethynylating agent, this excess acetylene can be present in the reaction medium utilized to convert the compound of formula II to the compound of formula I. On the other hand, additional acetylene can be utilized in carrying out this reaction.

The following examples are illustrative but not limitative of the invention. In the examples, all temperatures are in degrees Centigrade (°C.) and the ether utilized is diethyl ether.

EXAMPLE 1

Sodium (80 g.) was dissolved in liquid ammonia (1,500 ml.) and acetylene was passed through the solution until the blue color was discharged. While the passage of acetylene was continued anhydrous magnesium sulfate powder (100 g.) was added and the mixture was stirred for 2 hours. Diethyl ether (200 ml.) was added to the mixture followed by a solution, at −15°C. to −19°C., of methyl vinyl ketone (189 g.) in diethyl ether (600 ml.) the addition taking 12 minutes. The acetylene flow was stopped, the ammonia was evaporated and when the residue reached −20°C. it was dropped into a solution of 98% by weight aqueous sulfuric acid (200 ml.) in water (1,250 ml.) which was maintained at −5°C. to +5°C. The etheral layer was separated and the aqueous phase was extracted with diethyl ether (2 × 200 ml.). The combined etheral solutions were washed with saturated brine (80 ml.) and saturated sodium bicarbonate solution (20 ml.), then the ether was removed by distillation at atmospheric pressure. Distillation of the residue gave 3-methyl-pent-1-en-4-yn-3-ol (174 g.) b.p. 31°–37°C./18 mmHg (yield 67%).

EXAMPLE 2

Using the procedure of Example 1, but replacing the magnesium sulfate with anhydrous magnesium fluoride (52 g.), 3-methyl-pent-1-en-4-yn-3-ol was obtained in 44% yield.

EXAMPLE 3

Using the procedure of Example 1, but replacing the magnesium sulfate with anhydrous magnesium chloride (80 g.) 3-methyl-pent-1-en-4-yl-3-ol was obtained in 61% yield.

EXAMPLE 4

Sodium (60 g.) was dissolved in liquid ammonia (1,200 ml.) and acetylene was passed through the solution until the blue color was discharged. With continued passage of acetylene at a slow rate a solution of ethyl magnesium bromide in diethyl ether, (prepared from magnesium (24 g.), diethyl ether (440 ml.) and ethyl bromide (109 g.)), was then added and the mixture was stirred for an hour. A solution, at −10°C. to −19°C., of methyl vinyl ketone (189 g.) in diethyl ether (600 ml.) was introduced over 20 minutes, then the acetylene flow was stopped and the ammonia was evaporated. When the residue reached −20°C., it was dropped into a solution of sulfuric acid (350 ml.) in water (1,250 ml.) at −5°C. to +5°C. The ethereal layer was separated and the aqueous phase was extracted with diethyl ether (2 × 200 ml.). The combined ethereal solutions were washed with a mixture of saturated brine (80 ml.) and saturated sodium bicarbonate solution (20 ml.) then dried over anhydrous sodium sulfate. The diethyl ether was removed from the extracts by distillation at atmospheric pressure using a 1 ft. × 1 in. Goodloe column. The residue on distillation yielded 159 g. of 3-methyl-pent-1-en-4-yn-3-ol b.p. 34°C./20 mmHg. The yield was thus 61.3%.

EXAMPLE 5

Using the procedure of Example 1, but replacing the methyl vinyl ketone with benzal acetone (146 g.) and using sodium (30 g.) and magnesium sulfate (40 g.), a product b.p. 118°C./1 mmHg was obtained. This product was shown to contain benzal acetone (25.7 g.) and 3-methyl-1-phenyl-pent-1-en-4-yn-3-ol (117.4 g.). The conversion of the former was thus 82.4% and the yield of the latter was 82.9%.

EXAMPLE 6

Using the procedure of Example 1, but replacing the methyl vinyl ketone with crotonaldehyde (170 g.) hex-4-en-1-yn-3-ol (171.4 g.), b.p. 63°–65°C./20 mmHg, was obtained. The yield was thus 73.5%.

EXAMPLE 7

Using the procedure of Example 1, but replacing the methyl vinyl ketone with mesityl oxide (309 g.) a distillate, b.p. 67°–90°C./50 mmHg was obtained. The distillate contained mesityl oxide (154.0 g.) and 3,5-dimethyl-hex-4-en-1-yn-3-ol (97.9 g.). The conversion of the former was thus 45.6% and the yield of the latter 59.6%.

EXAMPLE 8

Preparation of Ethynylating Agents

Sodium (80 g.) was dissolved in liquid ammonia (1500 ml.) and acetylene was passed through the solution until the blue color was discharged. Anhydrous magnesium sulfate (200 g.) was now added and the resultant suspension was stirred for 4 hours. The suspended material was isolated by filtration using diatomaceous earth as a filter aid. The filter cake was washed by slurrying with liquid ammonia in the filter funnel. The cake was then sucked dry by application of vacuum and then dried in a stream of nitrogen at 50°C. and approximately 600 mmHg to yield a white powder.

EXAMPLE 9

A portion of the white solid prepared in Example 8 (200 g.) was suspended in liquid ammonia (1000 ml.) and stirred for about an hour. A solution of methyl vinyl ketone (35 g.) in diethyl ether (250 ml.) was cooled to −20°C. and added to the suspension over approximately 5 minutes. The mixture was stirred for 2 hours, the ammonia was evaporated with the aid of steam and when the temperature of the residue reached +5°C., it was dropped into a solution of aqueous sulfuric acid (90% by weight), (60 ml.) in water (700 ml.). The organic layer was separated and the aqueous layer was extracted with diethyl ether (2 × 100 ml.). The combined ethereal solutions were washed with a mixture of saturated aqueous sodium bicarbonate solution (20 ml.) and saturated aqueous sodium chloride solution (40 ml.), then dried over anhydrous sodium sulfate. The ether was removed by distillation and the residue (31.6 g.) contained 3-hydroxy-3-methyl-pent-1-en-4-yne.

What is claimed is:

1. The process of forming an ethynylating agent comprising mixing under substantially anhydrous conditions from about 10% to about 95% by weight of sodium acetylide with from about 5% to about 95% by weight of an anhydrous magnesium compound selected from the group consisting of magnesium sulfate, magnesium chloride, magnesium fluoride, aryl magnesium halide, lower alkyl magnesium halide and cycloalkyl magnesium halide said weight percent being based upon the total weight of magnesium in said magnesium compound and sodium acetylide; said mixing being carried out in the presence of liquid ammonia at a temperature of from −100°C. to 100°C. and a pressure of from 15 psia to 1000 psia.

2. The process of claim 1 wherein said mixture is formed with 40% to 60% by weight of said sodium acetylide and 40% to 60% by weight of magnesium in said magnesium compound, said weight % being based upon the total weight of magnesium in said magnesium compound and sodium acetylide.

3. The process of claim 1 wherein said magnesium compound is magnesium sulfate.

4. The process of claim 1 wherein said magnesium compound is magnesium chloride.

5. The process of claim 1 wherein said magnesium compound is ethyl magnesium bromide.

* * * * *